US012697046B1

(12) United States Patent
Ahmad et al.

(10) Patent No.: US 12,697,046 B1
(45) Date of Patent: Aug. 4, 2026

(54) BODILY FLUID ANALYSIS SYSTEM CAPABLE OF ASSESSING EFFECT OF GUT HEALTH ON WEIGHT LOSS OR OTHER HEALTH PROGRAM

(71) Applicant: Invoy Holdings Inc., Irvine, CA (US)

(72) Inventors: Lubna M. Ahmad, Irvine, CA (US);
Priyadarshini Singha, Orange, CA (US); Marcus James Goudie, Irvine, CA (US)

(73) Assignee: invoy Holdings Inc., Irvine, CA (US)

( * ) Notice: Subject to any disclaimer, the term of this patent is extended or adjusted under 35 U.S.C. 154(b) by 0 days.

(21) Appl. No.: 18/329,412

(22) Filed: Jun. 5, 2023

(51) Int. Cl.
| | |
|---|---|
| *A61B 5/08* | (2006.01) |
| *A61B 5/083* | (2006.01) |
| *G16H 20/60* | (2018.01) |
| *G16H 40/67* | (2018.01) |
| *G16H 50/30* | (2018.01) |
| *A61B 10/00* | (2006.01) |

(52) U.S. Cl.
CPC ............. *A61B 5/083* (2013.01); *G16H 20/60* (2018.01); *G16H 40/67* (2018.01); *G16H 50/30* (2018.01); *A61B 2010/0087* (2013.01)

(58) Field of Classification Search
CPC ........................ A61B 5/083; A61B 2010/0087; G16H 20/60; G16H 40/67; G16H 50/30
See application file for complete search history.

(56) References Cited

U.S. PATENT DOCUMENTS

| | | | |
|---|---|---|---|
| 6,609,068 B2 | 8/2003 | Cranley et al. | |
| 9,351,684 B1 | 5/2016 | Ahmad et al. | |
| 10,736,548 B2 | 8/2020 | Ahmad et al. | |
| 10,782,284 B1 * | 9/2020 | Ahmad ................ | G01N 33/497 |
| 11,103,157 B2 | 8/2021 | Gupta et al. | |
| 11,170,662 B2 | 11/2021 | Ahmad et al. | |

(Continued)

OTHER PUBLICATIONS

Suntrup, Donald J., et al. "Characterization of a High-Resolution Breath Acetone Meter for Ketosis Monitoring." medRxiv, Cold Spring Harbor Laboratory Press, Jan. 1, 2020, www.medrxiv.org/content/10.1101/2020.04.20.20072975v1.full. Accessed Dec. 16, 2023. (Year: 2020).*

(Continued)

*Primary Examiner* — Tse W Chen
*Assistant Examiner* — Michael A Catina
(74) *Attorney, Agent, or Firm* — Knobbe, Martens, Olson & Bear, LLP

(57) ABSTRACT

A breath analysis system includes a breath analysis device that measures acetone, and a gut biomarker such as methane and/or hydrogen, in breath of a participant in a weight loss or other health program. The system includes one or more processors that use the measurements to assess the progress of the participant. For example, the system may use the gut biomarker measurements to assess whether the measured acetone level accurately represents fat metabolism. As another example, the system may determine, based on changes in acetone and gut biomarker levels, whether a diet change is producing a gut health issue that adversely affects the body's ability to metabolize fat. The system may also generate diet/nutritional recommendations. Embodiments are also disclosed in which some or all of the analyzed analytes are measured in the participant's blood rather than in breath.

15 Claims, 7 Drawing Sheets

(56) References Cited

U.S. PATENT DOCUMENTS

| 11,250,942 | B1 | 2/2022 | Ahmad et al. |
| 2003/0031625 | A1* | 2/2003 | Lin ..................... A61K 31/445 |
| | | | 424/9.1 |
| 2013/0288208 | A1 | 10/2013 | Yamada et al. |
| 2017/0332951 | A1* | 11/2017 | Ahmad ................. G16H 50/20 |
| 2019/0178868 | A1 | 6/2019 | Shortt et al. |

OTHER PUBLICATIONS

Fox, Maggie. "A Breath Test Might Show It's Not Your Fault You're Fat." NBCNews.Com, NBCUniversal News Group, Mar. 26, 2013, www.nbcnews.com/health/body-odd/breath-test-might-show-its-not-your-fault-youre-fat-flna1C9078875. Accessed Dec. 29, 2023. (Year: 2013).*

Schwarm, K.K., Strand, C.L., Miller, V.A et al. Calibration-free breath acetone sensor with interference correction based on wavelength modulation spectroscopy near 8.2 μm. Appl. Phys. B 126, 9 (2020). (Year: 2020).*

Chakraborty et al., "Detection of biomarker in breath: A step towards noninvasive diabetes monitoring," Current Science, vol. 94, No. 2, Jan. 2008, pp. 237-242.

Kundu et al., "Breath Acetone Analyzer: Diagnostic Tool to Monitor Dietary Fat Loss," Clinical Chemistry, vol. 39, No. 1,1993, pp. 87-92.

Mathew et al., "Technologies for Clinical Diagnosis Using Expired Human Breath Analysis," Diagnostics, vol. 5, No. 1, 2015, pp. 27-60.

* cited by examiner

BODILY FLUID ANALYSIS SYSTEM CAPABLE OF ASSESSING EFFECT OF GUT HEALTH ON WEIGHT LOSS OR OTHER HEALTH PROGRAM

BACKGROUND

Technical Field

The present invention relates to devices and systems for measuring and analyzing analyte levels in exhaled breath, and for providing associated messaging and recommendations for health program participants.

Description of the Related Art

Portable breath analysis devices exist for allowing individuals to measure their breath acetone levels. These devices are sometimes provided to participants in health programs, such as weight loss programs, to enable the program participants to monitor fat metabolism. The present inventors have facilitated the breath acetone devices communicating wirelessly with a mobile application that runs on the program participant's smartphone or other mobile communications device. In such systems, the mobile application may use the analyte measurements, in combination with user-supplied data from the program participant, to provide messaging and recommendations to the participant. For example, the mobile application may provide feedback to the participant regarding the effectiveness of a diet and may recommend modifications to the diet. In some systems pioneered by the present inventors, for example, messaging and recommendations may also be provided by human health coaches who remotely monitor the progress of program participants via a network portal.

DETAILED DESCRIPTION OF PREFERRED EMBODIMENTS

Figure 1:
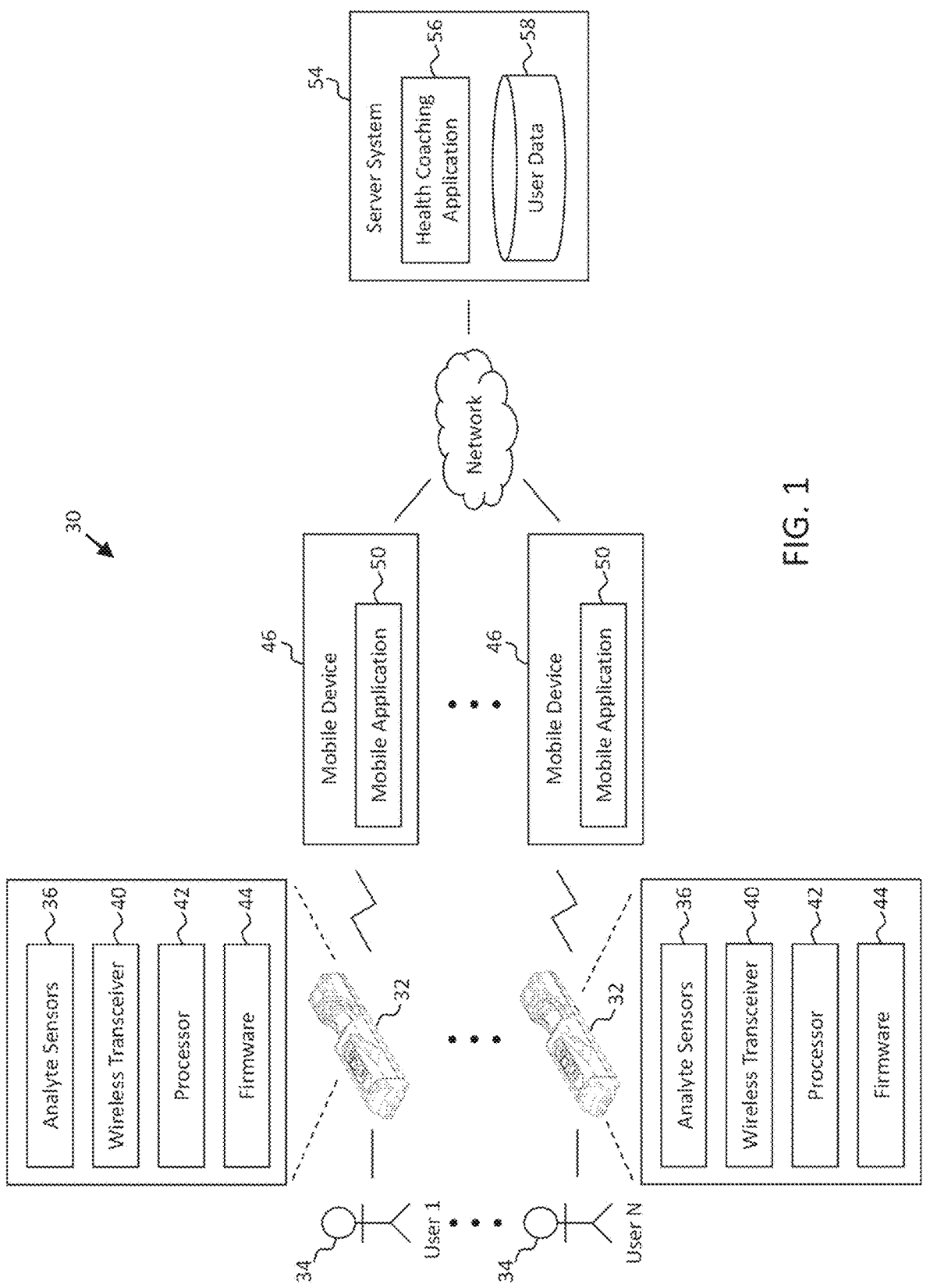
FIG. 1 illustrates the primary components of a breath analysis system according to one embodiment.

It is desirable for diet and nutrition programs to address not only metabolic factors but also factors impacting digestion, adsorption, gut health/gut dysbiosis and with an understanding of the state of the gut microbiome.

Some background is useful here. The gut microbiome is involved in various daily operations of the human body. The microbiome is comprised of millions of microorganisms (sometimes referred to as microbes or microbiota) of multiple different species or types. Some of these include viruses, bacteria, parasites and fungi. These microorganisms can appear throughout the body but are most heavily concentrated, typically, in the large intestine and the small intestine.

The microbiome is generally unique to each individual and evolves over time. One of the first exposures of the individual to microorganisms is during birth and then through breast milk. Thereafter, environmental and other factors, including, without limitation, disease, medication and diet, will impact the microbiome.

There is a general concept of symbiosis that typically exists between the person and the microbiome. Whether it is "good" or "bad" bacteria (sometimes referred to as symbiotic and pathogenic bacteria), in a normal, healthy individual, there is a state of symbiosis and the microbiome coexists "peacefully" with the individual. However, dysbiosis can also occur for a variety of reasons, including disease, changes to diet, antibiotics, major environmental changes and the like. In response to the dysbiosis, the individual may begin to feel ill for reasons that are exacerbated by the gut dysbiosis.

A properly functioning symbiotic gut synthesizes (in some cases entirely uniquely) vitamins and amino acids, breaks down toxic foods and absorbs nutrients. Factors impacted by the gut include, without limitation, the presence or absence of vitamin B series, particularly B12, and vitamin K, short chain fatty acids (SCFA), and the breakdown and digestion of complex carbohydrates like starches and fibers. Increasingly we are learning the relationships between vitamin B12 and gut health as well as the strong correlative effect between SCFA and maintenance of normal glucose and cholesterol levels.

Generally, but not exclusively, pathogenic bacteria are present in lower PH (acidic) environments. One way to combat the growth of pathogenic bacteria is with the addition of high fiber foods, which tends to suppress the low acidity.

Factors that can directly or indirectly impact the gut microbiome include: (a) natural prebiotics such as those found in bananas, seaweed, asparagus, onions and garlic, (b) starches that have prebiotics like oats, barley and whole grains, and (c) fermented foods that contain probiotics like yogurt with live active cultures, pickled vegetables, kombucha, sauerkraut and kefir.

The interrelationship between gut health and related biomarkers, including metabolic biomarkers such as acetone, has been surprisingly understudied. The present inventors have evaluated sensors, systems, and methods to optimize nutrition, diet and general health based on optimizing metabolic factors while also considering the reality of gut health or the state of some or all of the gut microbiome. The term "gut biomarker" refers to any biomarker that is present as a result of, or is reflective of the state of, the gut microbiome, including the microbiota themselves and byproducts, such as methane and hydrogen. Methane, hydrogen, hydrogen sulfite and C-reactive protein are examples of gut biomarkers that can be measured in exhaled breath. In some cases a gut biomarker may be based on a combination of analytes measured in exhaled breath and/or another bodily fluid; for example, a gut biomarker may be calculated as a weighted or non-weighted average, or as a sum, of methane and hydrogen concentrations in exhaled breath.

One example of a gut heath issue is small intestinal bacterial overgrowth, or SIBO. Gut health issues can adversely affect an individual's progress on a weight loss program in various ways. For example, in some cases, when a program participant is placed on a diet that is low in carbohydrates and is intended to increase fat metabolism, the transition to the new diet, which lowers insulin levels, causes the participant to develop a gut health issue. The existence of the gut heath issue may impair the body's ability to metabolize fat, resulting in poor weight loss results. The gut health issue may additionally or alternatively produce symptoms, such as nausea, bloating, diarrhea, abdominal pain, or loss of appetite, that discourage the individual from continuing the program.

Another problem with existing systems and processes is that they commonly fail to adequately consider the impact of the participant's digestive state on their ketone levels. For example, in some cases a participant's ketone (e.g., acetone) level may appear lower than expected because the participant is still digesting a meal; as a result, the feedback provided to the participant may be unnecessarily negative even though the participant has adhered to their diet.

Some embodiments of the present invention address these and other issues by providing a breath analysis system that, in addition to measuring and analyzing breath acetone levels, measures and analyzes one or more additional breath analytes, such as methane, hydrogen and/or hydrogen sulfite, that individually or collectively serve as one or more gut biomarkers. (As discussed below, some or all of the analyte measurements may alternatively be generated by analyzing the blood of the participant.) A computer-based system analyzes the measurements of the multiple analytes in combination to assess a program participant's progress on a weight loss or other health program. As one example, the system may assess whether a participant's inability to attain elevated breath acetone levels is potentially the result of a gut heath issue. When the system detects a possible gut health issue, the system (or a human health coach) may provide messaging and associated recommendations that seek to address the issue; for example the system may vary the participant's diet using an algorithm that seeks to maintain breath acetone at an elevated level while reducing methane and/or hydrogen (and/or other gut biomarkers) to an acceptably low level.

Methane is produced by methanogenic bacteria in the digestive tract. High methane levels can indicate an imbalance in gut microbiome, and are commonly associated with such disorders as constipation, bloating, and irritable bowel syndrome. Hydrogen is an important analyte associated with bacterial overgrowth (including SIBO) and irritable bowel syndrome, and can also indicate an intolerance to lactose, fructose or sucrose. Both methane and hydrogen cross into the blood and are carried to the lungs where they can be exhaled in breath.

In addition to being gut biomarkers, methane and hydrogen levels can be useful for interpreting the acetone levels of an individual who is not experiencing a gut health issue. For example, if an individual performs a breath test upon waking up in the morning, the methane and/or hydrogen level can be used to assess the participant's digestive state, such as by predicting the amount of time since the participant last ate. As discussed below, this information, in combination with the individual's current acetone level, is useful for determining the individual's level of fat metabolism.

Gut biomarkers are most commonly measured in stool samples and the present focus in primarily in exhaled breath. However, in other body fluids, such as blood, there are either direct or indirect measurements of gut health. For example, C-reactive protein may be present in blood in higher concentrations during gut dysbiosis. Additionally, other protein markers such as zonulin, calprotectin and A1AT may be present in the blood where the pattern may be associated with leaky gut syndrome, further indicating challenges with gut health. Other blood-based gut biomarkers, and particularly biomarkers for gut dysbiosis, include zonulin, lipopolysaccharide-binding protein, soluble CD14, bactericidal/permeability-increasing protein, peptidoglycan, serum lipopolysaccharide (LPS), intestinal fatty acid-binding protein (I-FABP), zonulin, and D-lactate. Urine-based gut biomarkers for gut dysbiosis include altered bacterial composition, e.g., increased pro-inflammatory Enterobacteriaceae and reduced protective bacteria against autoimmune and inflammatory processes, including butyrate and urolithin-producing bacteria (Lachnospiraceae members and Gordonibacter). Thus, although the present disclosure focuses on the use of breath to measure gut biomarkers, in some embodiments the gut biomarker(s) may additionally or alternatively be measured in another bodily fluid, such as blood or urine.

II. Example System Environment

FIG. 1 illustrates the primary components of a breath analysis and health coaching system 30 according to one embodiment. The system 30 includes portable breath analysis devices 32 that are provided to respective health program participants 34 or "users." The health programs typically include diets that seek to achieve a desired level of fat metabolism, and may also include other program components, such as exercise components. The health programs are preferably customized for the particular users by human health coaches and/or software routines, and may be modified over time as discussed below.

Each breath analysis device 32 preferably includes analyte sensors 36 for sensing acetone, and at least one of methane and hydrogen, in breath exhaled by the user into the device's mouthpiece. For example, each breath analysis device 32 may include a first analyte sensor that senses acetone, and a second analyte sensor that senses methane and/or hydrogen. In some embodiments, the breath analysis devices may measure additional or alternative gut biomarkers.

The analyte sensors 36 may, for example, be metal oxide semiconductor (MOS) sensors. The acetone sensor may alternatively be a colorimetric sensor of the type described in U.S. Pat. No. 11,504,099, the disclosure of which is hereby incorporated by reference, or may be electrochemical enzymatic sensors. Although each breath analysis device 32 preferably includes multiple analyte sensors 36, in some embodiments a single analyte sensor may be used to measure all of the analytes of interest (e.g., acetone and methane, or acetone, methane and hydrogen).

The participants 34 are typically instructed to perform a breath test upon waking up each morning, or according to another regular schedule. Preferably, each breath analysis device 32 is capable of measuring acetone, and methane and/or hydrogen (or any other gut biomarker(s)) in a single exhaled breath sample; however, in some embodiments, users may be asked to perform separate breath tests for measuring different analytes. The analyte sensors 36 are positioned along a flow path that extends between the mouthpiece and an exhaust port (not shown), as is known in the art. In some embodiments, rather than exhaling into a mouthpiece, the user may exhale into a breath bag or other breath container that is thereafter attached to the breath analysis device 32 for analysis.

As shown in FIG. 1, each breath analysis device 32 also includes a wireless transceiver 40, such as a Bluetooth Low Energy transceiver, and a processor 42 that executes firmware code 44 stored in memory. The wireless transceiver 40 enables the breath analysis device 32 to communicate wirelessly with the respective user's smartphone or other mobile communications device 46. The mobile communications devices 46 runs a mobile application 50 that provides various types of functionality for enabling users to track and interpret their analyte measurements and to obtain associated recommendations. The mobile application 50 may also provide functionality for interacting with a human health coach. Examples of types of functions that may be included in the mobile application 50 are described in U.S. Pat. Nos. 10,278,640 and 11,250,942, the disclosures of which are hereby incorporated by reference.

As further shown in FIG. 1, each instance of the mobile application 50 communicates over a network with a remote server system 54, which may include one or more physical computers that execute software. The mobile applications 50 report various types of user data 58, including analyte measurements and user responses to questions, to the server system 54. The server system 54 preferably runs a health coaching application 56 that uses the user data 58 to select personalized messaging and recommendations to provide to the respective users. The personalized messaging and recommendations may be provided directly to the respective users via the mobile application 50 or may be communicated to the users by a human health coach. In some embodiments, the health coaching application 56 may use artificial intelligence algorithms to select or generate the personalized messaging and recommendations, as described in U.S. Pat. No. 11,170,662, the disclosure of which is hereby incorporated by reference. The messaging and recommendations may also be generated, in whole or in part, by human heath coaches or administrators; for example, a human health coach may select between multiple health coaching recommendations generated by the health coaching application 56, and the coach-selected recommendation may then be communicated to the user.

The system shown in FIG. 1 may be modified in various ways. As one example, some or all program participants may wear a device (e.g., an arm patch having a sensor that extends through the skin) that operates as a continuous ketone monitoring device and/or a continuous glucose monitoring device, as is known in the art. This wearable device may also measure one or more blood analytes, such those mentioned above, that are gut biomarkers. The blood analyte measurements generated by such a device may be wirelessly transmitted by the wearable device to the mobile application 50 and used in the algorithms described herein. In some embodiments, all of the analytes measured and analyzed by the system may be measured in the patient's blood by such a wearable device, in which case the breath analysis device may be omitted.

The various computer algorithms and processes described herein may be implemented within health coaching application 56, the mobile application 50, the firmware executed by the breath analysis device 32, or any combination thereof.

III. Detecting Gut Health Issues Caused by Diet Changes

Figure 2:
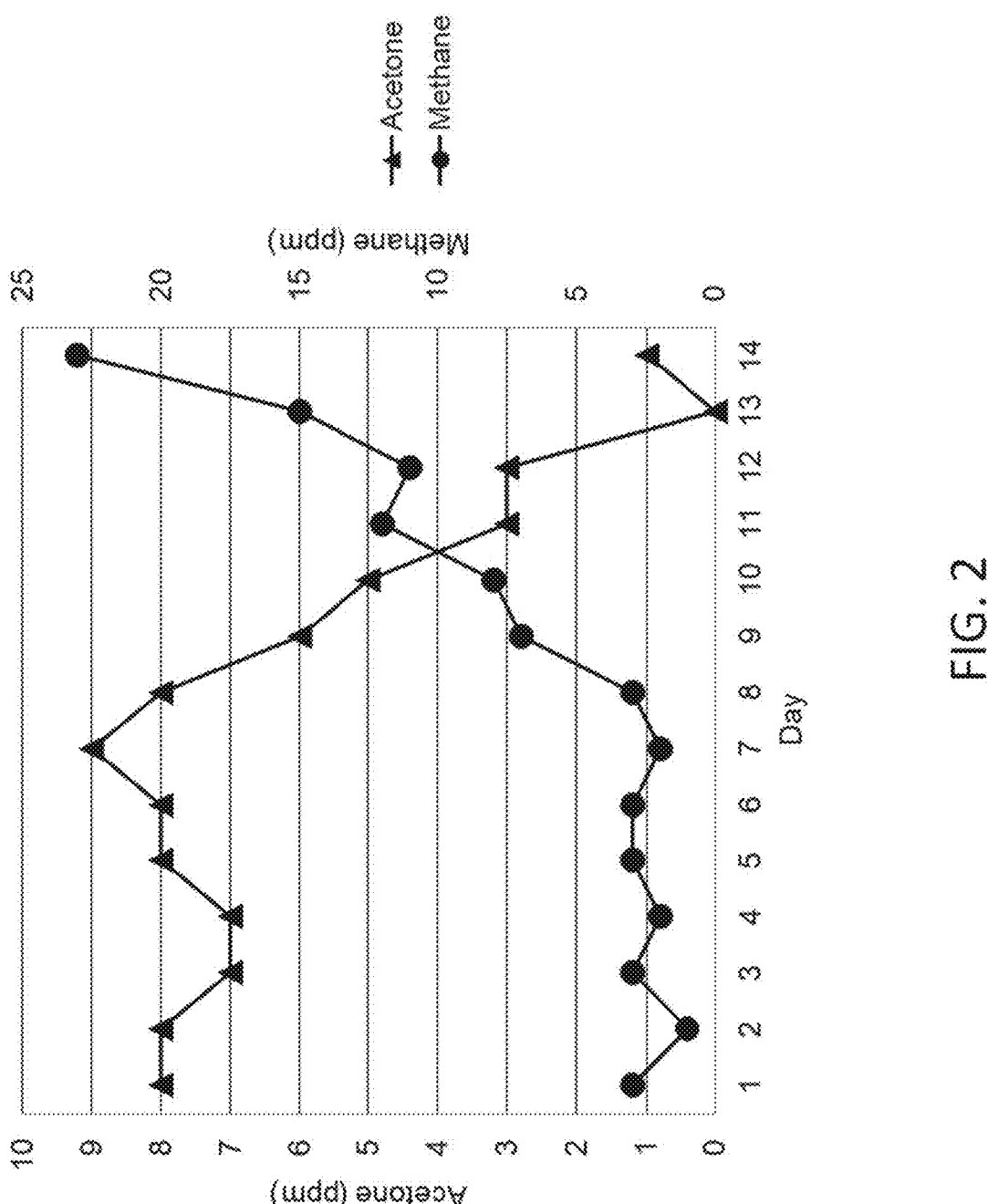
FIG. 2 illustrates analyte levels over time of a health program participant whose diet is causing a gut health issue that adversely affects the body's ability to metabolize fat.

In some cases, a participant's transition to a low-carb or other diet may cause the participant to develop a gut health issue that adversely affects the body's ability to metabolize fat. FIG. 2 illustrates this scenario. The participant in this example has just transitioned to a low carb diet and is performing a breath test daily, such as upon waking up in the morning. The downward trending graph shows the participant's breath acetone level in parts per million (ppm). The upward trending graph represents the participant's methane level, hydrogen level, or an average of both, also in ppm. For ease of discussion, it will be assumed that the upward trending graph represents the methane level.

In this example, the individual initially has an elevated acetone level (as is desirable for losing weight) and has a low methane level, suggesting that no gut health issues exist. A breath acetone level above 7 ppm may be considered elevated. A breath methane or hydrogen level below 2 ppm may be considered low, and above 6 ppm may be considered high. Beginning on Day 8, the individual's acetone level begins to gradually decrease while the methane level begins to gradually increase. A drop in acetone by 4 or 5 ppm may be considered significant. By Day 13 or 14, the individual has an elevated methane level but a low acetone level. This pattern in which the methane level increases while the acetone level drops indicates that the individual's diet may be creating distress to the gut and digestive system, and that this distress is adversely affecting fat metabolism. When this situation is detected, the system 30 may recommend one or more gut restoration therapies, such as consumption of dietary fiber or probiotics.

The system may thereafter continue to monitor the individual's acetone and methane (and/or hydrogen or other gut biomarker) levels to assess whether the recommendation addresses the issue. The system may also recommend additional interventions if the gut health issue persists; for example, the system may recommend that the participant avoid processed sugars, avoid dairy, or transition to a FODMAP diet. If these interventions are not effective, the system may thereafter recommend that the individual be placed on a course of antibiotics, as discussed below.

Figure 3:
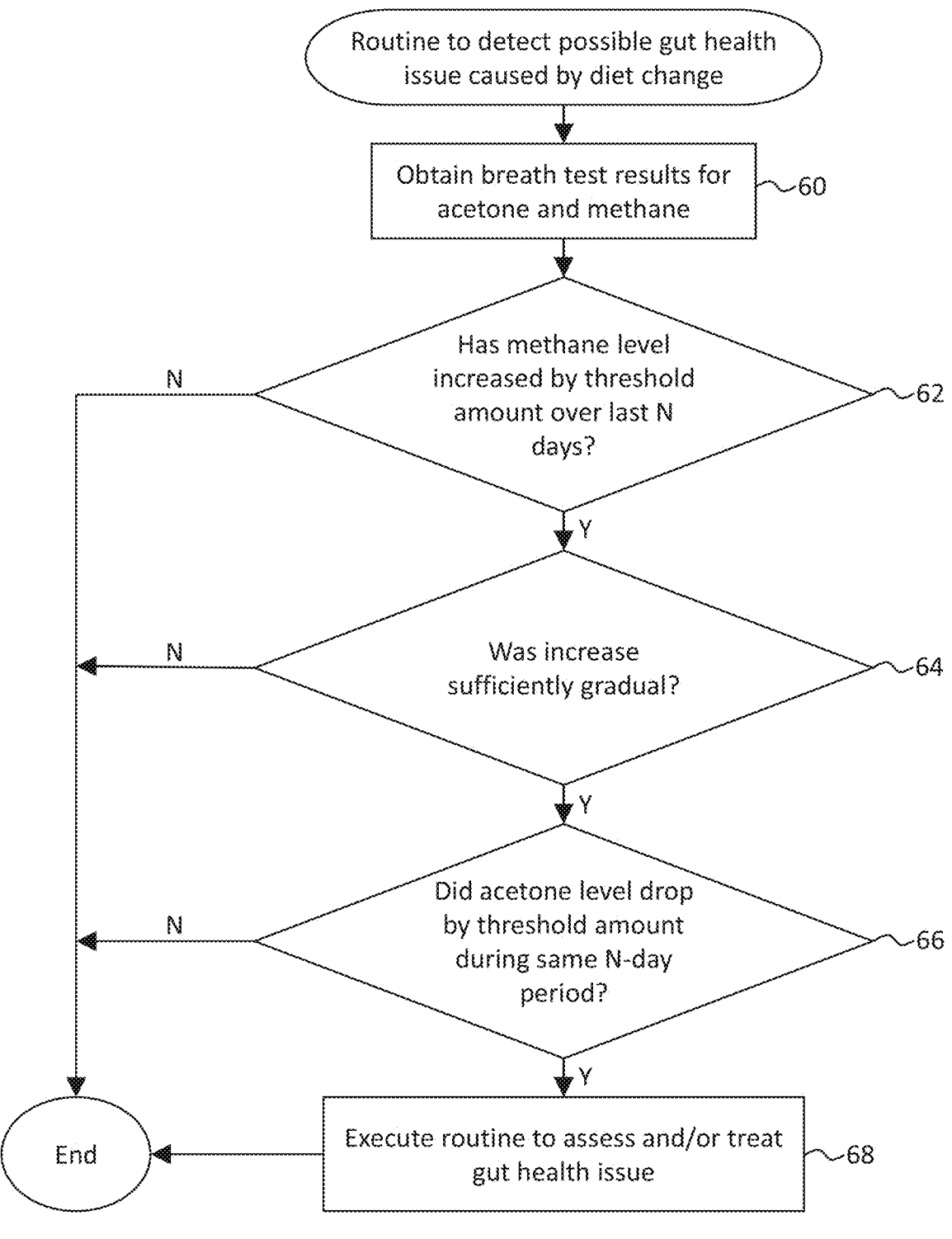
FIG. 3 illustrates a computer process for detecting conditions of the type shown in FIG. 2.

FIG. 3 illustrates a process that may be executed periodically, such as each time a user performs a breath test during a defined period following a diet change, to assess whether the diet change has caused a gut health issue of the type illustrated by FIG. 2. This routine may be executed by the user's mobile device 46 (e.g., smartphone), by the server system 54, by the breath analysis device 32, and/or by any other processing node. It is assumed in this example that the user performs the breath test daily using a device 32 that measures the concentrations of at least acetone and methane. As will be recognized, the process may be modified to use hydrogen levels in place of, or in addition to, methane levels, and/or to use another gut biomarker.

In block 60, the process obtains the latest breath test results, including the acetone and methane concentration measurements. In some cases, the breath test results may also include user-supplied data that may be used to adjust and/or interpret the measurements. For example, the user may be asked when they ate their last meal, whether they feel sick, whether they have exercised, whether they have adhered to the diet, etc.

In block 62, the process analyzes the methane measurements collected over the last N days to determine whether the methane concentration has increased by at least a threshold amount. The value of N may, for example, be 4, 5, 6, 7, 8 or 9, and the methane threshold may, for example, be a value in the range of 4 to 8 PPM (e.g., 6 PPM). Moving averages of the methane measurements, such as 2-point, 3-point or 4-point moving averages, may be calculated and used for purposes of this determination.

If the threshold test of block 62 is positive, the process in block 64 assesses whether the increase was sufficiently gradual to be the result of the body's adaptation to the diet change. If, for example, the increase in the methane concentration occurred (or occurred primarily) in just one or two days, the increase is more likely the result of something other than the diet change, such as the user being sick. The process may determine whether the increase was sufficiently gradual in any of a number of ways, such as by (1) determining whether the increase occurred over three or more days, (2) calculating the slope of the methane curve and comparing the slope to a threshold, and/or (3) determining whether the methane measurement increased by more than a threshold amount, such as 3 or 4, in a single day. User collected data may also be considered during this step; for example, if the user reported being sick, the process may use different thresholds. In some embodiments, block 64 may be omitted.

If the methane increase is determined in block 64 to be sufficiently gradual, in block 66 the process determines whether the user's acetone level decreased by a threshold amount, such as 4 or 5 PPM, during the same N-day period. Such a drop in acetone is an indication that a gut health issue, and particularly a buildup of bad bacteria, possibly exists that is impairing the body's ability to metabolize fat.

If the determination in block 66 is positive, the process executes a routine to assess and/or treat the possible gut health issue caused by the diet change. For example, the process may output a recommendation to the user to add dietary fiber or a probiotic to their diet, or to use another gut restorative therapy. The process may additionally or alternatively ask the user a series of questions to better assess the possible gut health issue; for example the user may be asked whether they have had cravings for sweets, as is a common symptom of a buildup of bad bacteria in the gut.

Once a gut restorative therapy is recommended, the system 30 continues to monitor the user's analyte levels to determine whether the therapy is effective. As discussed below, the system may also suggest various diet changes and restorative therapies over time to seek a diet that produces both an elevated acetone level and acceptably low methane and/or hydrogen levels.

Figure 4:
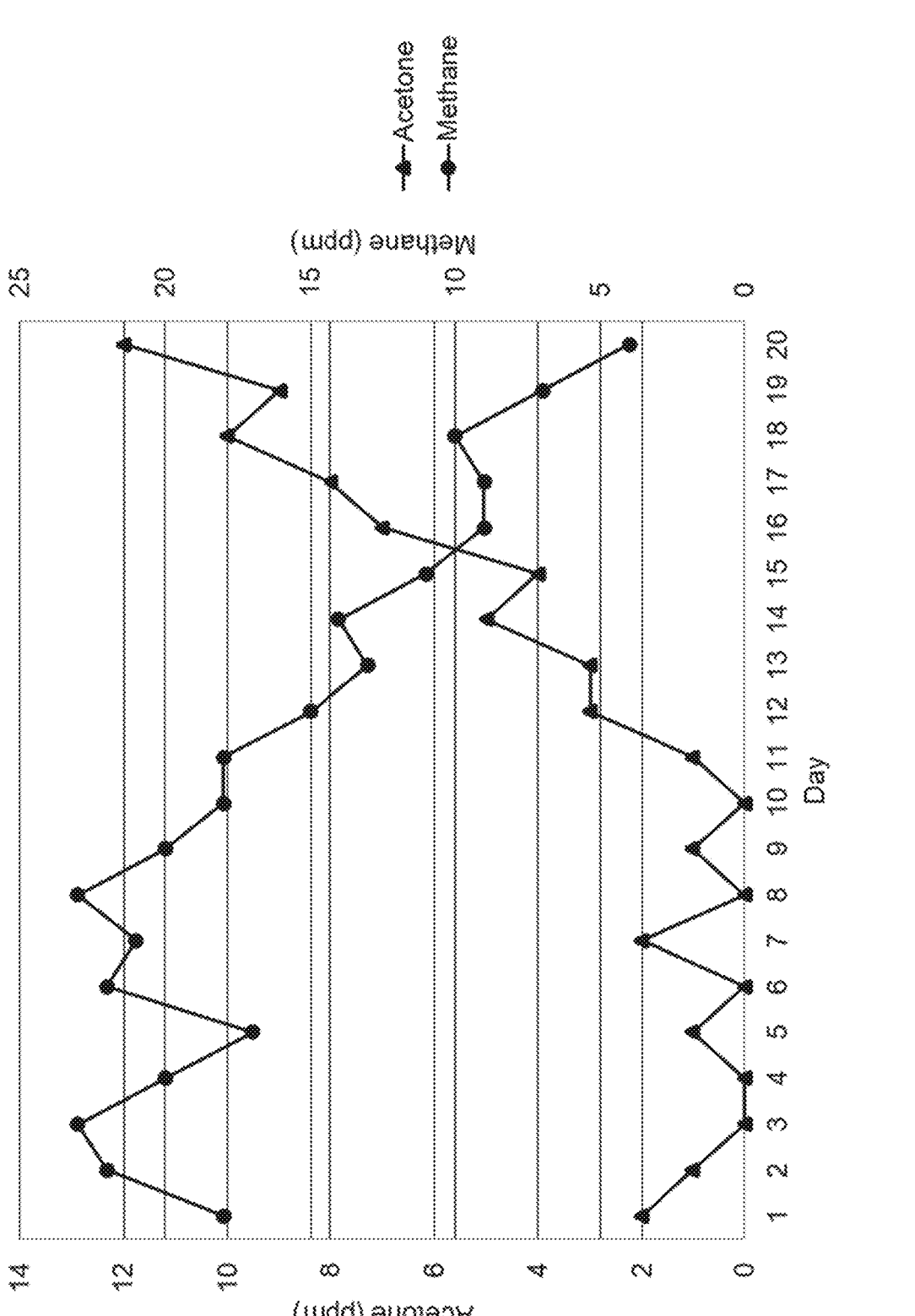
FIG. 4 illustrates analyte levels over time of a program participant before and after the participants begins a ten-day course of antibiotics to treat a detected gut health issue.

In some cases, the system may recommend a course of antibiotics to address a significant gut health issue. FIG. 4 illustrates this scenario. In this example, the individual's acetone level is low even though their self-reported level of carbohydrate restriction is very consistent and reliable. In addition, the individual's methane level is very high. These levels suggest that the gut is out of equilibrium with body and the body is no longer effectively absorbing nutrients, resulting in impaired glucose and cholesterol levels and creating temporary resistance to insulin. The imbalance in this example is not necessarily the result of a diet change.

At Day 10, the individual is placed on a ten-day course of antibiotics, causing the methane level to drop. This reduction can vary considerably from person to person; in some cases the gut health issue is completely resolved (as in this example), and in others the reduction may be closer to 50%. If the treatment is effective (as in this example), the individual's fasting glucose levels, cholesterol and LDL improve, and so do the breath acetone levels. Typically, the effectiveness of the treatment persists long after user completes the course of antibiotics. In some cases, before and after glucose tolerance tests may be performed to assess the effectiveness of the treatment. The graphs shown in FIG. 4 may also be representative of scenarios in which the participant's gut health issue is treated using something other than antibiotics (e.g., probiotics).

IV. Using Methane/Hydrogen Levels to More Effectively Interpret Acetone Levels

After eating the last meal of the day, an individual's methane level slowly declines over a roughly 6-to-12-hour period as the body digests the meal. The duration of this decline can vary from person to person, and also typically depends on what the user ate. During the same time period, the individual's acetone level gradually increases toward its post-meal peak. This post-meal peak is a useful indicator of the body's level of fat metabolism.

For an individual who consistently performs a breath test at the same time each morning before eating, their acetone level is more likely to be near its peak if they consumed their last meal relatively early (e.g., at 5 PM). Thus, an individual's methane level in the morning can be informative in assessing whether their measured acetone level accurately reflects the body's level of fat metabolism.

In some embodiments, the system 30 takes advantage of this negative correlation between post-meal methane and acetone levels to interpret an individual's acetone measurement more accurately. More specifically, the system uses the measured methane level to assess whether, or the extent to which, the measured acetone level is an accurate or valid indicator of fat metabolism. In some embodiments, the system may also use the measured methane and acetone levels to predict the peak acetone level, and/or to adjust the acetone measurement to compensate for the body's digestive state. In some cases, this task may involve using the methane level to predict the timing of the individual's last meal.

Table 1 illustrates the morning breath test results of two individuals, Subject A and Subject B. Subject A desirably has an elevated acetone level and a low methane level. The low methane level suggests that Subject A did not eat a late last meal. In this scenario, the system, via the mobile application 50, would provide positive feedback to the user (e.g., "great job!" or "you are burning fat").

TABLE 1

|  | Acetone AM | Methane AM |
| --- | --- | --- |
| Subject A | 4.3 | 2.1 |
| Subject B | 1.8 | 9.2 |

Subject B, on the other hand, has a relatively low acetone level and an elevated methane level. The elevated methane level suggests that subject B had a late last meal, and that the acetone level may not accurately reflect the level of fat metabolism. The system 30 may address this scenario in various ways. For example, the mobile application 50 may prompt the user to confirm that they had a late last meal, and/or may ask the user whether they ate something out of the ordinary. The system, via the mobile application 50, may additionally or alternatively provide feedback that reflects the high methane level. The following are examples: "Your acetone level is low, but this may be the result of having a late last meal yesterday," or "We adjusted your acetone level to 4.2 to reflect your late last meal—you are doing great!".

Figure 5:
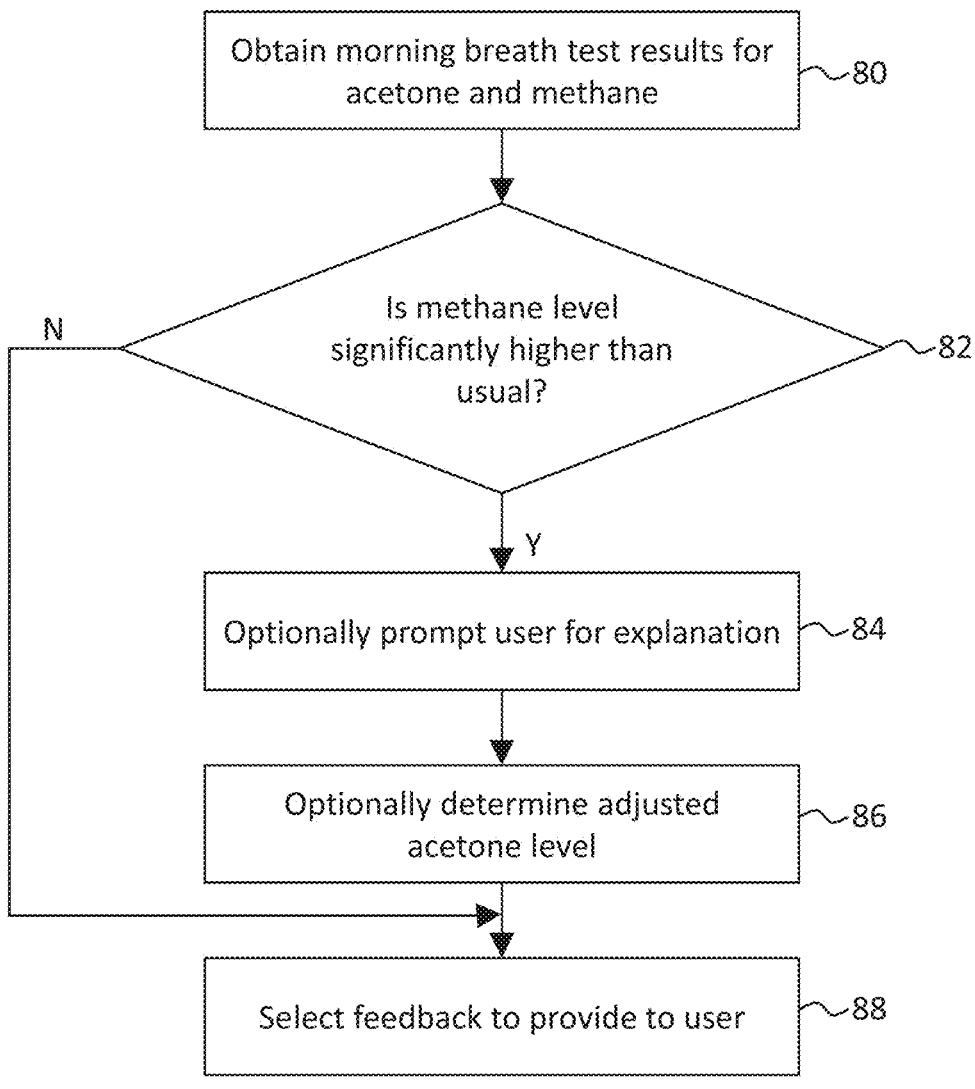
FIG. 5 illustrates a process for analyzing and interpreting morning analyte measurements.

FIG. 5 illustrates a process that may be implemented by the system 30 (e.g., via executable code of the mobile application 50 and/or the health coaching application 56) to analyze morning breath test results. In block 80, the process obtains the breath test results for acetone and methane. As with the previous examples, the breath hydrogen level may be obtained and analyzed in place of, or in addition to, the methane level. In block 82, the process determines whether the methane level significantly higher than usual. This may involve comparing the methane measurement to a threshold, which may or may not be user specific. An example, of a non-user-specific threshold is 3 ppm or 4 ppm. A user-specific threshold may be determined by taking the average of some or all of the user's prior morning methane measurements and by adding a value, such as 1 PPM, to account for normal variations; for example, if the user's average morning methane level is 2.3, a threshold of 3.3 may be used to determine whether the current methane level is significantly higher than usual.

If the methane level is significantly higher than usual, in block 84, the system optionally prompts the user for an explanation. For example, as mentioned above, the mobile application 50 may prompt the user to confirm that they had a late last meal, and/or may ask the user when they ate their last meal. The system may also ask the user whether they ate something out of the ordinary. Any such information provided by the user may incorporated by the system into the feedback provided to the user.

In block 86, the system optionally determines an adjusted (boosted) acetone level that reflects the higher than usual methane level. The adjusted acetone level may be calculated in various ways. For example, data regarding the typical rate of change of methane and acetone may be used to predict what the acetone level would have been had the individual consumed the last meal at a usual time. Alternatively, if sufficient data has been collected for this particular user, user-specific data regarding such rates of change may be used. As part of this process, the system may optionally predict the timing of the last meal or may use a user-supplied indication of such timing. The timing of the last meal may be estimated using user-specific or non-user-specific data that correlates methane levels with time since last meal; such user-specific data may be generated for an individual by prompting the user over a period of time (e.g., the first two weeks of participation) to enter the time of their last meal, and correlating such time entries with the associated morning methane measurements.

As one example, a lookup table (which may or may not be user specific) may initially be used to map the measured methane level to the predicted number of hours since the last meal. If this time period is significantly shorter than usual (e.g., by 2 hours or more), the system may treat the measured acetone level as being lower than it would have been if the user had consumed the meal at a more typical time. The system may also use a second look up table (which may or may not be user specific) that maps the predicted time period to a compensation factor, and may use this compensation factor to determine an adjusted or normalized acetone level that is a prediction of what the acetone level would have been had the user consumed the meal at a usual time.

In block 88, the system selects or generates feedback to provide to the user via the mobile application 50. If the methane level was not determined to be elevated in block 82, this feedback is preferably based on the assumption that the user's actual acetone level accurately reflects their level of fat metabolism; thus, for example, if the acetone level is low (e.g., 2 ppm or lower), the mobile application 50 may notify the user that they are not metabolizing fat. If, on the other hand, the methane level was determined to be elevated in block 82, the system takes the elevated level, and any associated user-supplied explanation, into consideration in selecting feedback. In some embodiments, the feedback may include an adjusted acetone level (if such an adjusted level is calculated), or may include feedback that is selected based on this adjusted level (e.g., an indication that the individual is burning fat even though their unadjusted acetone level suggests otherwise).

V. Adaptive Adjustment of Diet to Achieve Participation Sustainability

Figure 6:
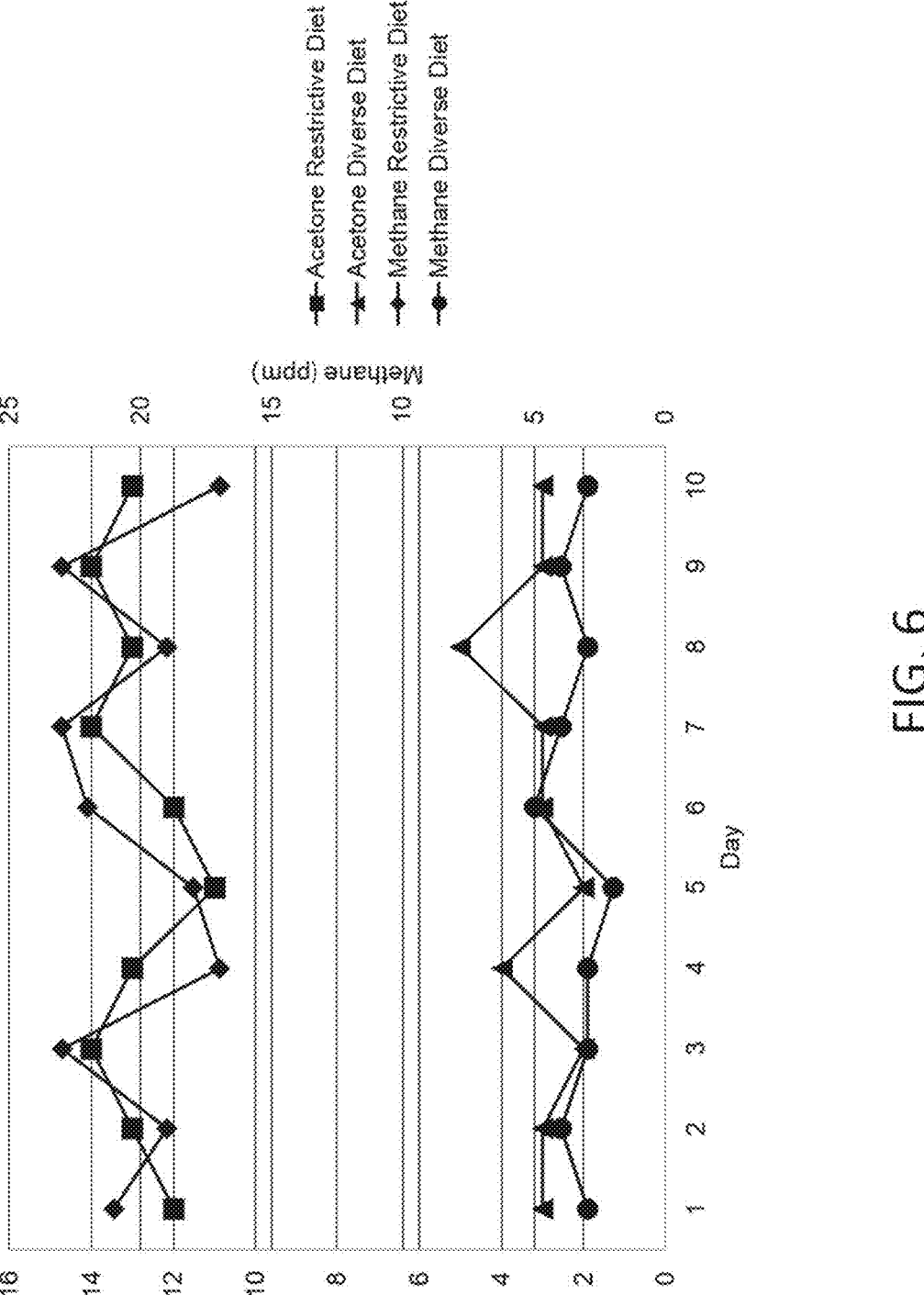
FIG. 6 illustrates analyte levels of the same individual while on two different diets.

As mentioned above, although weight loss programs typically seek to achieve high breath acetone levels, the diets that achieve the highest acetone levels sometimes lead to digestive stress, causing participants to discontinue the program. FIG. 6 illustrates this issue. The two graphs at the top show an individual's acetone and methane levels while the individual is on a highly restrictive diet. The two graphs at the bottom show the same individual's acetone and methane levels while the individual is on a more diverse diet.

Although the breath acetone levels are higher on the restrictive diet, the methane level is also elevated, suggesting digestive stress. Although the subject experiences fat metabolism on a restrictive program, the increase in digestive stress could lead to less compliance in the long term, and reversal of any weight loss progress. On the other hand, while the breath acetone levels are lower in the diverse diet, the lower methane level suggests that diverse diet is more sustainable and comfortable for this individual.

Figure 7:
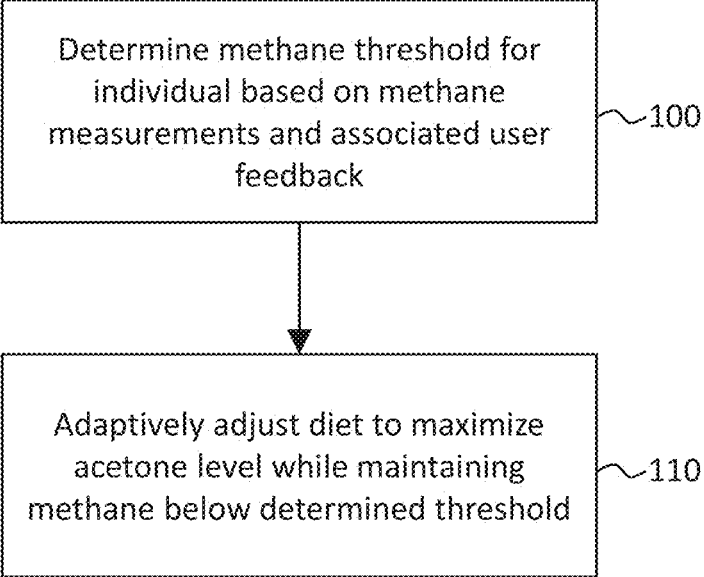
FIG. 7 illustrates a process for adaptively adjusting the diet of a participant so as to maximize acetone levels while maintaining a methane below a threshold level.

FIG. 7 illustrates one example of a process that may be implemented by the system 30 to seek a diet that produces elevated acetone levels while maintaining methane at an acceptable level. As with the preceding examples, the process can monitor hydrogen in place of, or in addition to, methane. In block 100, the process determines a methane threshold for a particular individual. This threshold is determined by correlating methane measurements over time with associated feedback from the individual on how they are feeling. For example, whenever a breath test produces an elevated or slightly elevated methane level (e.g., above 4 or 5 ppm), the mobile application 50 may ask the individual one or more questions about how they are feeling and record the associated responses. For example, the individual may be asked to indicate how they are feeling on a scale of 1 to 5, and/or may be asked whether they are experiencing specific symptoms such as nausea, bloating, diarrhea, loss of appetite, etc. Once enough data has been collected, the system may determine this individual's methane threshold. A non-user-specific methane threshold, such as 3 ppm, may alternatively be used, or may be used until sufficient data has been collected to determine a user-specific threshold.

In block 110, the system varies the individual's diet over time while monitoring the individual's acetone and methane levels. The system uses the data collected through this process to identify the diet that produces the highest acetone levels while maintaining methane below the identified methane threshold. Rather than seeking to maximize the acetone level, the process in block 110 may seek to identify one or more diets that maintain acetone above a target level. In some embodiments, the system select between various diet options using a machine learning algorithm that analyzes the data of many hundreds or thousands of users.

VI. Conclusion

All of the tasks and processes described above as being performed by "the system" may be performed under the control of program instructions executed by, e.g., (1) a server machine or group of machines of the server system 54, (2) a mobile device 46 of a user under control of the mobile application 50, (3) a breath analysis device 32, or (4) any combination of the foregoing. Each such computing machine or device typically includes a hardware processor (or multiple processors) that executes program instructions or modules stored in a memory or other non-transitory computer-readable storage medium or device (e.g., solid state storage devices, disk drives, etc.). The various functions disclosed herein may be embodied in such program instructions, and/or may be implemented in application-specific circuitry (e.g., ASICs or FPGAs) of the system. The server system 54 may include multiple computing devices or machines which may, but need not, be co-located. The results of the disclosed methods and tasks may be persistently stored by transforming physical storage devices, such as solid state memory chips and/or magnetic disks, into a different state. In some embodiments, the server system 54 system may be a cloud-based computing system.

Thus, the various disclosed processes and tasks may be implemented within a processing system that comprises one or more hardware processors, potentially including hardware processors of distinct machines, devices or network nodes.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

While the above detailed description has shown, described, and pointed out novel features as applied to various embodiments, various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others.

What is claimed is:

1. A breath analysis system, comprising:
   a breath analysis device including a sensor system comprising one or more sensors positioned along a flow path configured to measure, in a breath exhaled by a human subject, at least (1) acetone and (2) a gut biomarker; and
   a processing system comprising one or more hardware processors, the processing system configured to:
      receive measurements generated by the sensor system of at least acetone and the gut biomarker in the breath;
      determine a user-specific gut biomarker threshold for the gut biomarker based on a plurality of measurements of the gut biomarker received over a time period;
      use at least a measurement of the gut biomarker to make a determination of whether a measurement of acetone was generated at a point in time during which the human subject's breath acetone level corresponds to a level of fat metabolism in the human subject; and
      responsive to a determination that the measurement of acetone was generated at the point in time during which the human subject's breath acetone level corresponds to the level of fat metabolism:

select a diet plan from a plurality of diet plans that would maintain the human subject's breath acetone level at a target acetone level and below a maximum acetone level while maintaining the gut biomarker below the user-specific gut biomarker threshold, wherein the selected diet plan does not maximize acetone levels of the human subject; and
      output the selected diet plan.

2. The breath analysis system of claim 1, wherein the gut biomarker comprises at least one of methane or hydrogen.

3. The breath analysis system of claim 1, wherein the processing system is configured to determine whether the measurement of the gut biomarker indicates a digestive state that affects acetone levels.

4. The breath analysis system of claim 1, wherein the processing system is configured to determine whether the measurement of the gut biomarker indicates that an acetone level of the human subject has not yet peaked since the human subject last ate.

5. The breath analysis system of claim 1, wherein the processing system is configured to use the measurement of the gut biomarker to estimate a timing of a last meal consumed by the human subject.

6. The breath analysis system of claim 1, wherein the processing system is configured to use the measurement of the gut biomarker to generate an adjusted acetone measurement.

7. The breath analysis system of claim 1, wherein the processing system is configured to use the measurement of the gut biomarker, in combination with the measurement of acetone, to provide a feedback to the human subject regarding the level of fat metabolism.

8. The breath analysis system of claim 1, wherein the processing system comprises a hardware processor of a smartphone that communicates with the breath analysis device.

9. The breath analysis system of claim 1, wherein the processing system comprises a hardware processor of a server system.

10. The breath analysis system of claim 1, wherein the processing system comprises a hardware processor of the breath analysis device.

11. The breath analysis system of claim 1, wherein the one or more sensors comprises a first analyte sensor that measures an acetone concentration, and a second analyte sensor that measures a concentration of at least one of methane or hydrogen.

12. The breath analysis system of claim 1, wherein the processing system is configured to determine whether the measurement of acetone was generated at the point in time during which the human subject's breath acetone level corresponds to the level of fat metabolism in the human subject based on a post-meal negative correlation between the gut biomarker and acetone levels.

13. The breath analysis system of claim 1, wherein the processing system, in making said determination of whether the measurement of acetone was generated at the point in time during which the human subject's breath acetone level corresponds to the level of fat metabolism in the human subject, is configured to compare the measurement of the gut biomarker to the user-specific gut biomarker threshold.

14. The breath analysis system of claim 1, wherein the processing system is further configured to, responsive to the determination that the measurement of acetone was generated at the point in time during which the human subject's breath acetone level corresponds to the level of fat metabolism, use the measurement of acetone to provide a feedback to the human subject regarding the level of fat metabolism.

15. The breath analysis system of claim 1, wherein the processing system is further configured to provide a recommendation for one or more of consumption of dietary fiber, consumption of probiotics, avoiding processed sugars, avoiding diary, transition to a FODMAP diet, or being placed on a course of antibiotics.

\* \* \* \* \*